United States Patent
Kleyman et al.

(10) Patent No.: US 9,204,869 B2
(45) Date of Patent: Dec. 8, 2015

(54) ARTICULATION CONTROL MECHANISMS

(71) Applicant: Covidien LP, Mansfield, MA (US)

(72) Inventors: Gennady Kleyman, Brooklyn, NY (US); Eric Taylor, East Hampton, CT (US)

(73) Assignee: Covidien LP, Mansfield, MA (US)

( * ) Notice: Subject to any disclaimer, the term of this patent is extended or adjusted under 35 U.S.C. 154(b) by 112 days.

(21) Appl. No.: 13/735,079

(22) Filed: Jan. 7, 2013

(65) Prior Publication Data

US 2013/0178713 A1    Jul. 11, 2013

Related U.S. Application Data

(60) Provisional application No. 61/584,723, filed on Jan. 9, 2012.

(51) Int. Cl.
| | |
|---|---|
| *A61B 1/32* | (2006.01) |
| *A61B 17/02* | (2006.01) |
| *A61B 17/34* | (2006.01) |
| *A61B 17/29* | (2006.01) |

(52) U.S. Cl.
CPC .......... *A61B 17/0218* (2013.01); *A61B 17/0293* (2013.01); *A61B 17/3423* (2013.01); *A61B 2017/2908* (2013.01); *A61B 2017/2927* (2013.01); *A61B 2017/3405* (2013.01); *A61B 2017/345* (2013.01)

(58) Field of Classification Search
CPC ........... A61B 17/0218; A61B 17/3462; A61B 17/3421; A61B 17/3423
USPC ......... 600/141, 142, 146, 184–200, 201–246; 74/422, 89.11, 89.12, 89.16–89.16; 285/181, 184–185; 606/108
See application file for complete search history.

(56) References Cited

U.S. PATENT DOCUMENTS

| | | | | | |
|---|---|---|---|---|---|
| 1,607,662 | A | * | 11/1926 | Boynton | 175/228 |
| 1,626,782 | A | * | 5/1927 | Brooks | 137/577 |
| 1,750,953 | A | * | 3/1930 | Boynton | 175/267 |
| 2,333,802 | A | * | 11/1943 | Lowrey | 294/86.13 |
| 5,306,245 | A | | 4/1994 | Heaven | |
| 5,441,483 | A | | 8/1995 | Avitall | |
| 5,498,231 | A | * | 3/1996 | Franicevic | 600/190 |
| 5,501,654 | A | * | 3/1996 | Failla et al. | 600/204 |
| 5,549,637 | A | * | 8/1996 | Crainich | 606/207 |
| 5,607,095 | A | * | 3/1997 | Smith et al. | 227/177.1 |
| 5,725,536 | A | * | 3/1998 | Oberlin et al. | 606/139 |
| 5,797,537 | A | * | 8/1998 | Oberlin et al. | 227/176.1 |
| 6,068,621 | A | | 5/2000 | Balceta et al. | |
| 6,923,813 | B2 | | 8/2005 | Phillips et al. | |
| 7,540,872 | B2 | * | 6/2009 | Schechter et al. | 606/50 |
| 7,608,056 | B2 | | 10/2009 | Kennedy, II | |
| 7,682,319 | B2 | * | 3/2010 | Martin et al. | 600/585 |

(Continued)

*Primary Examiner* — Eduardo C Robert
*Assistant Examiner* — Jacqueline Johanas

(57) ABSTRACT

A surgical access port and method for achieving articulation is disclosed, the surgical access port including a housing, at least one lumen extending through the housing, and an articulation structure. The housing comprises an access member having a proximal end and a distal end, and defines a longitudinal axis. The lumen in the housing extends from the proximal to the distal end of the access member along the longitudinal axis. The articulation structure comprises a first tubular member and a second tubular member, the second tubular member hingably attached to the first tubular member, and an articulation element slidably attached to the first tubular member.

6 Claims, 8 Drawing Sheets

(56) References Cited

U.S. PATENT DOCUMENTS

| | | | |
|---|---|---|---|
| 7,811,277 B2* | 10/2010 | Boulais | 604/528 |
| 7,963,976 B2* | 6/2011 | Goldfarb et al. | 606/190 |
| 8,663,097 B2* | 3/2014 | Arai | 600/144 |
| 8,771,260 B2* | 7/2014 | Conlon et al. | 606/1 |
| 2002/0169362 A1* | 11/2002 | Kan et al. | 600/170 |
| 2003/0149422 A1 | 8/2003 | Muller | |
| 2005/0240193 A1 | 10/2005 | Layne et al. | |
| 2006/0094933 A1* | 5/2006 | Goldfarb et al. | 600/229 |
| 2006/0190028 A1* | 8/2006 | Wales et al. | 606/205 |
| 2006/0190032 A1* | 8/2006 | Wales | 606/205 |
| 2007/0049966 A1 | 3/2007 | Bonadio et al. | |
| 2007/0249908 A1* | 10/2007 | Lu et al. | 600/184 |
| 2007/0250110 A1 | 10/2007 | Lu et al. | |
| 2008/0147109 A1* | 6/2008 | Kambin et al. | 606/190 |
| 2009/0188965 A1* | 7/2009 | Levin et al. | 227/179.1 |
| 2009/0227843 A1* | 9/2009 | Smith et al. | 600/208 |
| 2010/0094091 A1* | 4/2010 | Cappola | 600/137 |
| 2010/0121147 A1 | 5/2010 | Oskin et al. | |
| 2010/0324375 A1* | 12/2010 | Piskun | 600/207 |
| 2011/0054479 A1* | 3/2011 | Aram et al. | 606/87 |
| 2011/0144444 A1* | 6/2011 | Sakai et al. | 600/206 |
| 2011/0245620 A1* | 10/2011 | Hamada | 600/219 |
| 2011/0251466 A1* | 10/2011 | Kleyman et al. | 600/208 |
| 2012/0041264 A1* | 2/2012 | Blase | 600/121 |
| 2012/0116398 A1* | 5/2012 | Goldfarb et al. | 606/49 |
| 2012/0253131 A1* | 10/2012 | Malkowski et al. | 600/201 |
| 2012/0253132 A1* | 10/2012 | Davis | 600/201 |
| 2012/0310220 A1 | 12/2012 | Malkowski et al. | |
| 2013/0178837 A1* | 7/2013 | Malkowski | 606/1 |
| 2014/0018826 A1* | 1/2014 | Viola | 606/142 |

* cited by examiner

ARTICULATION CONTROL MECHANISMS

CROSS-REFERENCE TO RELATED APPLICATIONS

This application claims the benefit of and priority to U.S. Provisional Patent Application No. 61/584,723, filed Jan. 9, 2012, the entire disclosure of which is incorporated by reference herein.

BACKGROUND

1. Technical Field

The present disclosure relates generally to surgical instruments for use with a seal anchor member. More particularly, the present disclosure relates to articulating surgical instruments usable with a seal anchor member that provides multiple instrument access through a single incision in a minimally invasive surgical procedure.

2. Description of Related Art

Increasingly, many surgical procedures are performed through small incisions in the skin. As compared to the larger incisions typically required in traditional procedures, smaller incisions result in less trauma to the patient. By reducing the trauma to the patient, the time required for recovery is also reduced. Generally, the surgical procedures that are performed through small incisions in the skin are referred to as endoscopic. If the procedure is performed on the patient's abdomen, the procedure is referred to as laparoscopic. Throughout the present disclosure, the term minimally invasive is to be understood as encompassing both endoscopic and laparoscopic procedures.

During a typical minimally invasive procedure, surgical objects, such as surgical access devices (e.g., trocar and cannula assemblies) or endoscopes, are inserted into the patient's body through the incision in tissue. In general, prior to the introduction of the surgical object into the patient's body, insufflation gas is used to enlarge the area surrounding the target surgical site to create a larger, more accessible work area. Accordingly, the maintenance of a substantially fluid-tight seal is desirable so as to inhibit the escape of the insufflation gas and the deflation or collapse of the enlarged surgical site. In response to this, various access devices with sealing features are used during the course of minimally invasive procedures to provide an access for surgical objects to enter the patient's body. Each of these devices is configured for use through a single incision or a naturally occurring orifice (i.e. mouth, anus, or vagina) while allowing multiple instruments to be inserted through the device to access the working space beyond the device.

During procedures employing multiple surgical instruments through a single incision access device, it is advantageous to coordinate the positioning of the end effectors of each surgical instrument. In situations where one or more of the surgical instruments is an articulating surgical instrument, manipulating the articulating surgical instrument or instruments to coordinate the positions of the end effectors is desirable.

One example, as disclosed by U.S. Pat. No. 5,520,678, uses control balls disposed in a proximal and distal end of a device, such that rotation and pivoting of the proximal control ball is transmitted to the distal control ball and consequently articulates an end effector at the distal end of the device.

Another example, as disclosed by U.S. Pat. No. 5,511,564, is a surgical device having a frame member with a pair of tissue holding mechanisms. An actuator mechanism allows positioning of the tissue holding mechanisms such that a portion of tissue can be stretched, providing a desirable surgical site.

Yet another example is disclosed in U.S. Pat. No. 5,269,772. A cannula assembly is disclosed having a tubular member configured to receive a laparoscopic instrument, as well as a second laparoscopic instrument such that both laparoscopic instruments are disposed at an angle in a body cavity and are used in conjunction to perform a laparoscopic surgery.

However, a continuing need exists for coordinating the end effectors of articulating surgical instruments used with an access device that permits multiple instruments to be used through a single incision.

SUMMARY

The present disclosure relates to surgical access ports for use in minimally invasive procedures where articulation of surgical instruments disposed in a body cavity is required.

According to one embodiment of the present disclosure, a surgical access port is provided which includes a housing, at least one lumen extending through the housing, and an articulation structure.

The housing includes an access member having a proximal end and a distal end, and defines a longitudinal axis. The lumen in the housing extends from the proximal to the distal end of the access member along the longitudinal axis.

The articulation structure includes a first tubular member and a second tubular member, the second tubular member hingably attached to the first tubular member, and an articulation element slidably attached to the first tubular member.

The articulation element of the present disclosure is envisioned to have multiple embodiments. In one embodiment, the articulation element will be a rigid member. This rigid member may have a mating surface that is configured to engage a mating surface disposed on the second tubular member. The mating surfaces, in one embodiment, will have gear teeth.

In another embodiment, the articulation element will be a flexible member. In this configuration, the flexible member may be fixably attached to a distal end of the second tubular member. In another embodiment, the flexible member will be configured such that it exerts a force at the distal end of the second tubular member that is opposite in direction to a force exerted by an operator at a proximal end of the flexible member.

The articulation structure may additionally contain a handle that extends proximally from the articulation element, through and above the proximal end of the access member.

In other configurations, the articulation element may be disposed either on the outside or inside of the tubular members.

The articulation structure is configured such that surgical instruments may be inserted therethrough.

Also disclosed is a method for achieving articulation of surgical instruments in a body cavity including inserting the surgical access port in a body member, inserting surgical instruments through the surgical access port, engaging the articulation structure such that a desired placement is achieved, and performing a minimally invasive procedure.

The method may also include removing the surgical instruments from the surgical access port, and removing the surgical access port from the body member.

The various aspects of this disclosure will be more readily understood from the following detailed description when read in conjunction with the appended drawings.

BRIEF DESCRIPTION OF DRAWINGS

Various embodiments of the presently disclosed articulating surgical access port are disclosed herein with reference to the drawings, wherein.

DETAILED DESCRIPTION OF EMBODIMENTS

Figure 1:
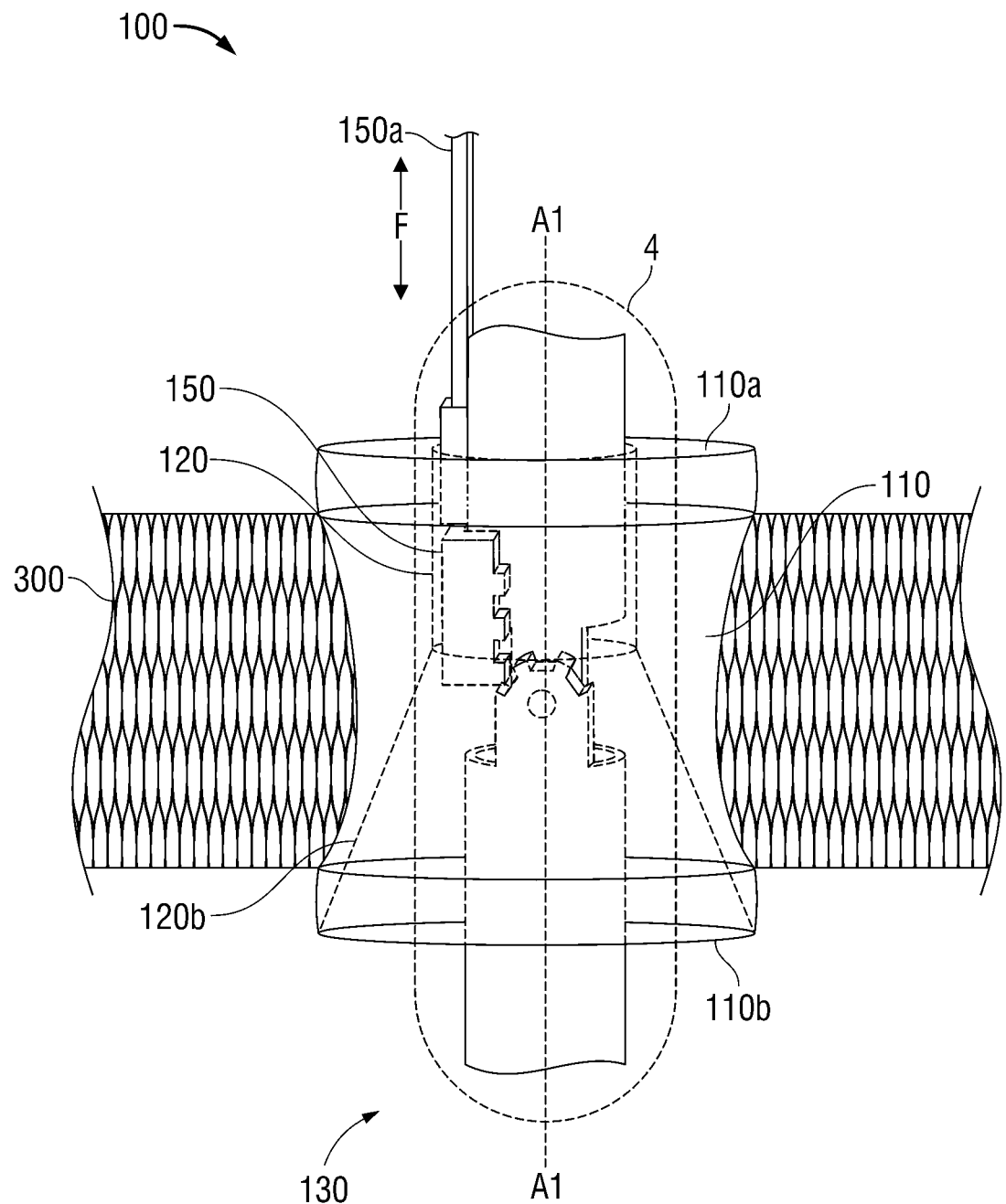
FIG. 1 is a side perspective view of an articulating surgical access port disposed in a layer of tissue and including a housing, an articulation structure, and a handle.

Referring initially to FIG. 1, a side perspective view of an articulating surgical access port 100 is shown disposed in a layer of tissue 300. The articulating surgical access port 100 includes an access member 110. The access member 110 may have a variety of shapes and profiles to fit a particular surgical site. In embodiments, the access member 110 may have a generally hourglass-shaped profile, and is formed of a compressible element suitable for contact with internal body surfaces, such as foam. The access member 110 has a proximal end 110a and a distal end 110b, and defines a longitudinal axis A1. The proximal and distal ends 110a,b of the access member 110 may include rims or flanges to assist in anchoring the surgical access port 100 in a layer of tissue 300.

Figure 2:
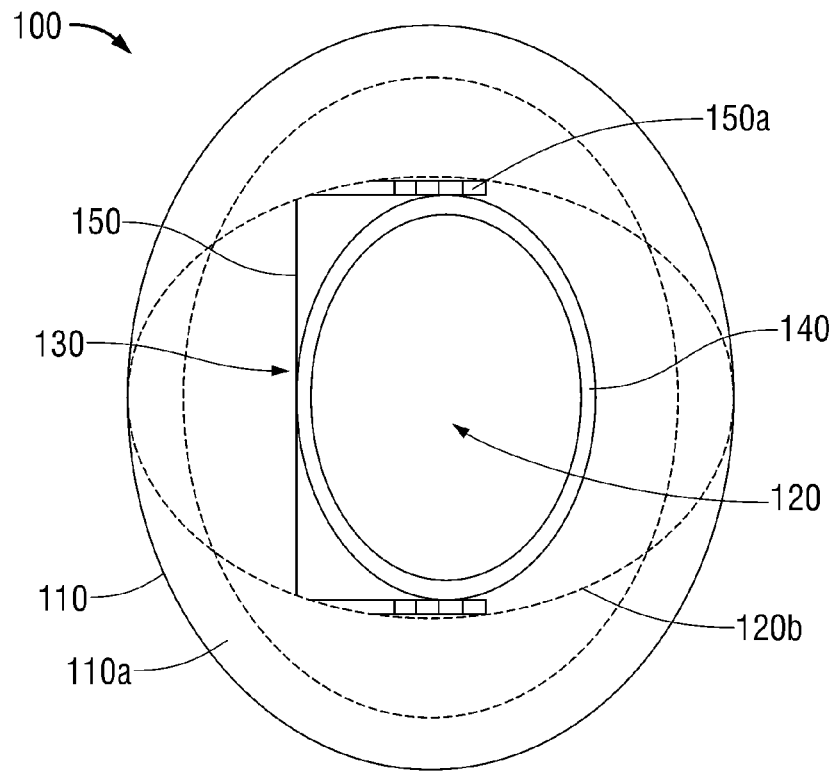
FIG. 2 is a top plan view of the surgical access port of FIG. 1.
Figure 3:
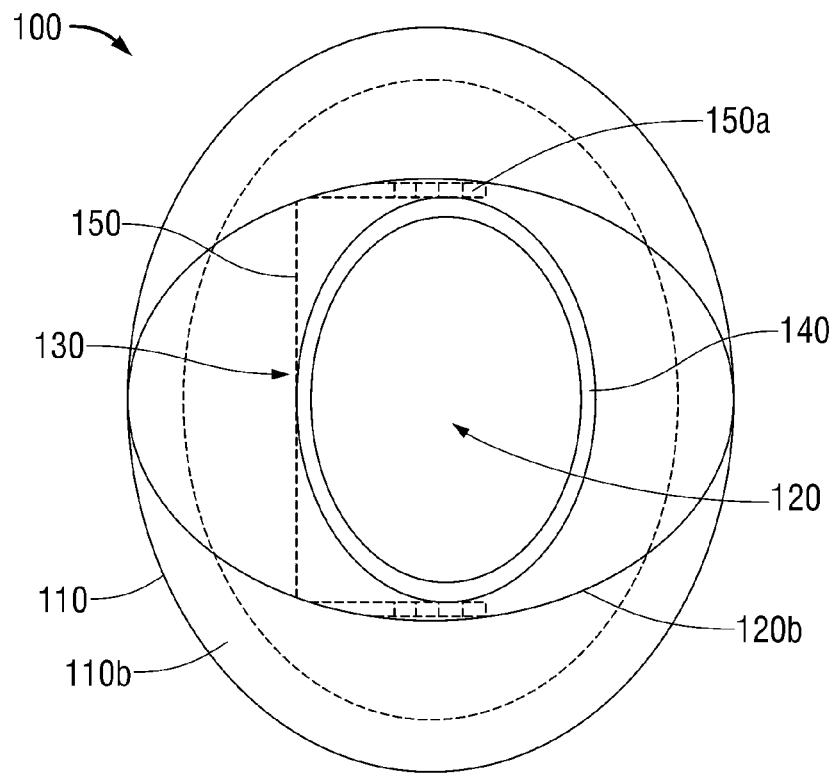
FIG. 3 is a bottom plan view of the surgical access port of FIG. 1.

Turning to FIGS. 2 and 3, the surgical access port 100 is shown in a top plan view and a bottom plan view, respectively. The access member 110 includes at least one lumen 120 that extends from the proximal end 110a of the access member 110, to the distal end 110b of the access member 110. The lumen 120 includes a lumen exit 120b. The lumen 120 is configured to widen toward the distal end 110b of the access member 110, such that the lumen exit 120b is slotted. Disposed within the at least one lumen 120 is an articulation element 130, shown in phantom view. The articulation element 130 (FIG. 5) is securely housed within the access member 110 such that the articulation element 130 (FIG. 5) will not separate from the access member 110 when external forces are applied to the articulation element 130.

Figure 4:
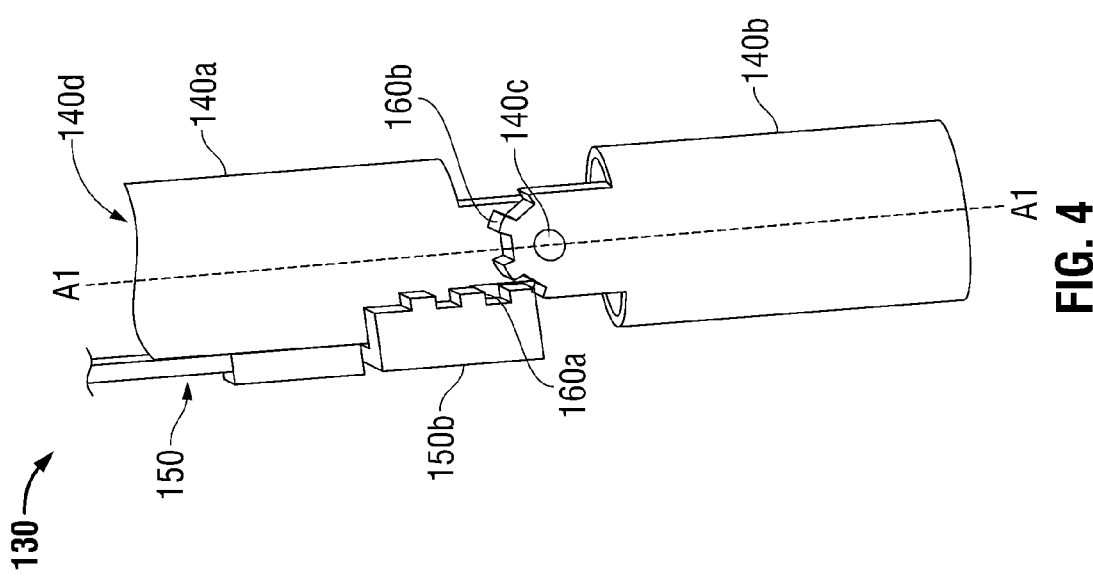
FIG. 4 is an enlarged side view of the articulation structure without the housing of the area of detail of FIG. 1.

Turning now to FIG. 4, a side profile of the articulation element 130 can be seen in detail. The articulation element 130 contains two tubular members 140a,b, with a first tubular member 140a disposed proximally of a second tubular member 140b. The tubular members 140a,b are hingably attached at a joint 140c that is typically a hinge, but in embodiments may be a ball-and-socket or other type connection so as to allow for rotation about at least one axis. The tubular members 140a,b define a channel 140d (FIG. 6) through which instruments may be passed.

The articulation element 130 contains a rigid pusher 150 that may further include a handle 150a (FIG. 5) that extends proximally above the proximal end 110a of the access member 110. The rigid pusher 150 is disposed on the tubular members 140 such that it is allowed a freedom of translation as shown by arrow "F" (FIGS. 1, 5-10) along the longitudinal axis A1. In FIG. 4, the rigid pusher 150 is disposed on an outer surface of the tubular members 140. In embodiments, the rigid pusher 150 may be otherwise disposed on the tubular members 140a,b, such as embedded within the walls of the tubular members 140a,b, or disposed on an interior surface of the tubular members 140a,b.

At a distal end 150b of the rigid pusher 150 is a first mating surface 160a. This first mating surface 160a is configured to engage a second mating surface 160b on tubular member 140b. The mating surfaces 160a, 160b are typically configured as teeth, as shown in FIG. 4, but in embodiments may be any complementary surface that allows for substantial engagement with the distal end 150b of the rigid pusher 150, such as a frictional or grooved surface. Additionally, the second mating surface 160b may be disposed on various locations of the outer surface of tubular member 140b. As shown in FIG. 4, the second mating surface 160b may be disposed around hinge 140c. In embodiments, the second mating surface 160b may be disposed on another portion of the second tubular member 140b.

Generally, distal end 150b of rigid pusher 150 is unrestricted in translation along the longitudinal axis A1. However, in embodiments, a stop or other mechanism may be employed to prevent overextension of the rigid pusher 150 beyond a desired location.

Figure 5:
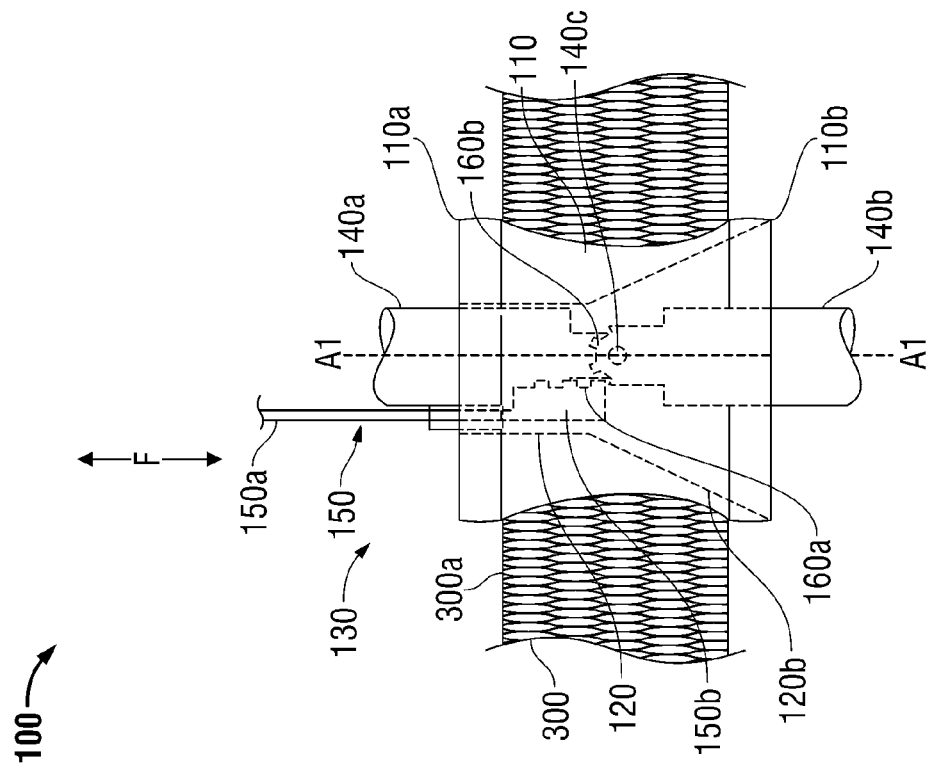
FIG. 5 is a side view of the articulating surgical access port disposed in a layer of tissue, with the articulation structure shown in phantom view.

Turning now to FIG. 5, a side view of the articulating surgical access port 100 is shown with the articulation structure 130 shown in phantom view. The rigid pusher 150 is shown disposed proximally of the hinge 140c. The distal portion 150b of the rigid pusher 150 is shown configured as a toothed rack, and in position to engage second mating surface 160b, shown clearly here as a toothed surface on the outer surface of joint 140c. Also shown here is a handle 150a, operatively connected to the distal end 150b of the rigid pusher 150. The handle 150a is configured such that it is disposed proximally of the proximal end 110a of the access member 110 (and thus external of a body surface 300a), and can be readily engaged by an operator of the articulating surgical access port 100. Also shown is lumen 120, widening toward the distal end 110b of the access member 110 and terminating at lumen exit 120b.

Figure 6:
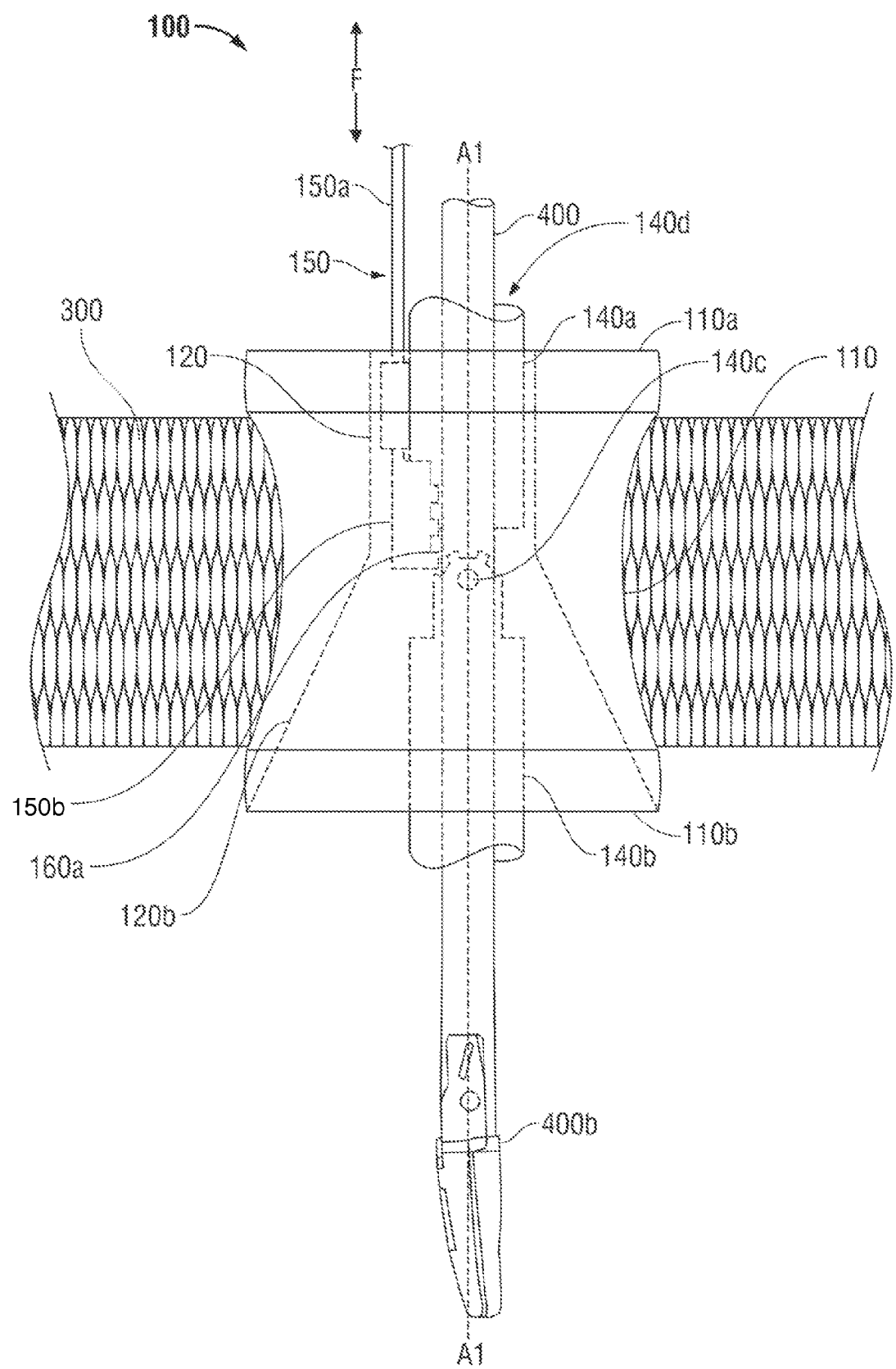
FIG. 6 is a side view of the articulating surgical access port disposed in a layer of tissue with a surgical instrument inserted through the articulation structure, both the articulation structure and surgical instrument shown in phantom view.

Referring to FIG. 6, the articulating surgical access port 100 is shown with a surgical instrument 400 disposed therethrough (shown in phantom view). The surgical instrument 400 is deformable, yet resilient, and is configured to withstand the forces exerted by the tubular members 140a,b during articulation. At a distal end of the surgical instrument 400 is an end effector 400b.

When the operator of the articulating surgical access port 100 engages the handle 150a and applies downward force on the rigid pusher 150 in the direction of the longitudinal axis A1, the rigid pusher 150 translates distally in the direction of the longitudinal axis A1.

The distal translation of the rigid pusher 150 ultimately results in engagement of the first and second mating surfaces 160a,b Further forcing the rigid pusher 150 will cause the second tubular member 140b to pivot about an axis substantially transverse to the longitudinal axis A1 and disposed through the joint 140c.

Figure 7:
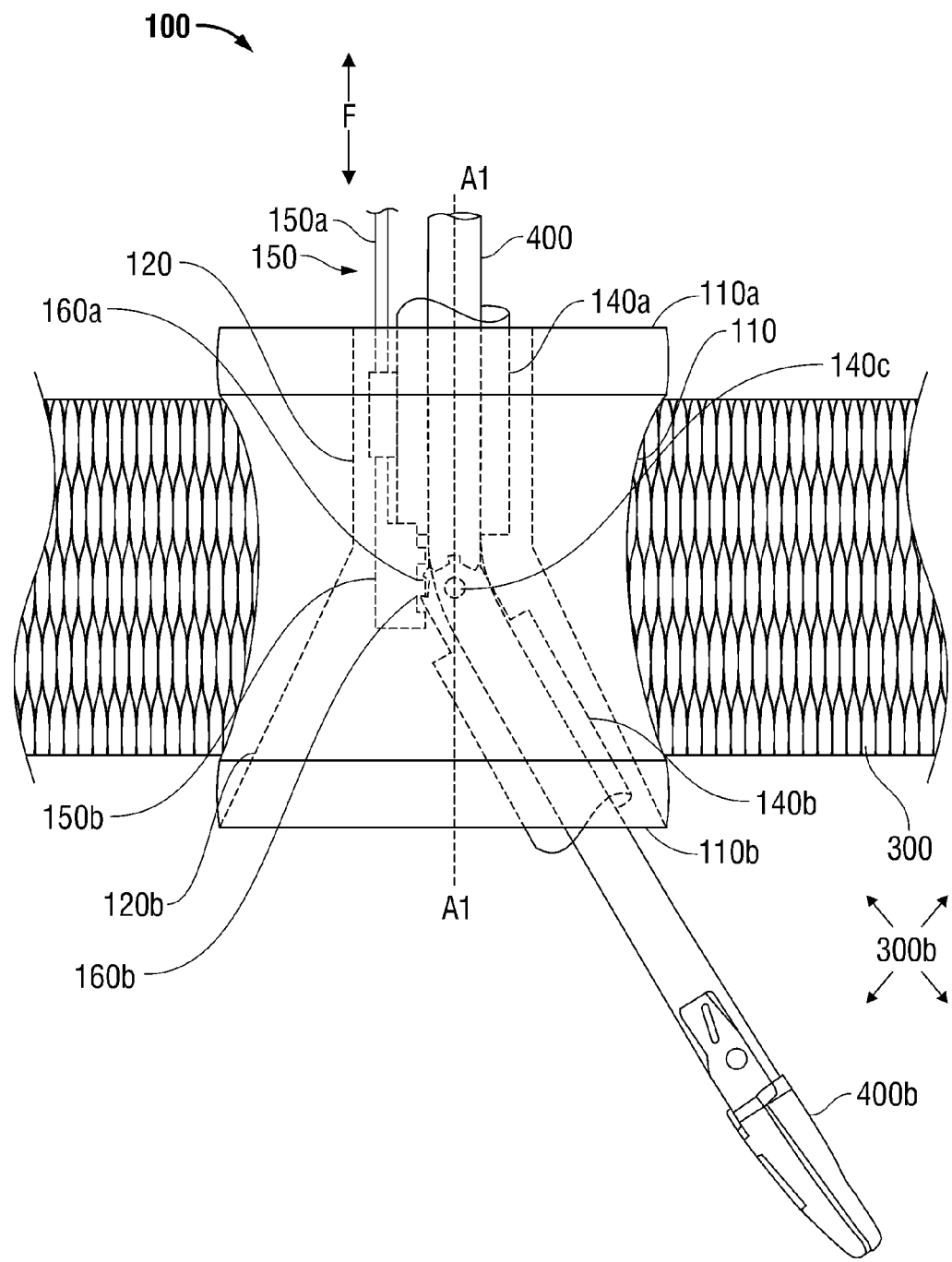
FIG. 7 is a side view of the articulating surgical access port disposed in a layer of tissue with a surgical instrument inserted through the articulation structure, shown in phantom view, with the articulation structure having been engaged and the surgical instrument deflected in response.

Turning now to FIG. 7, the articulating surgical access port 100 is shown with the rigid pusher 150 having been engaged by an operator, and the second tubular member rotated about an axis running through the joint 140c. The surgical instrument 400, disposed therethrough, is shown deflected in response to the forces exerted by the tubular members 140a,b.

The lumen 120 allows for the freedom of movement of the second tubular member during articulation. Additionally, the widened lumen exit 120b at the distal end 110b of the access member 110 allows the surgical instrument 400 and the end effector 400b to reach points in an internal body cavity 300b laterally spaced from the longitudinal axis A1.

Figure 8:
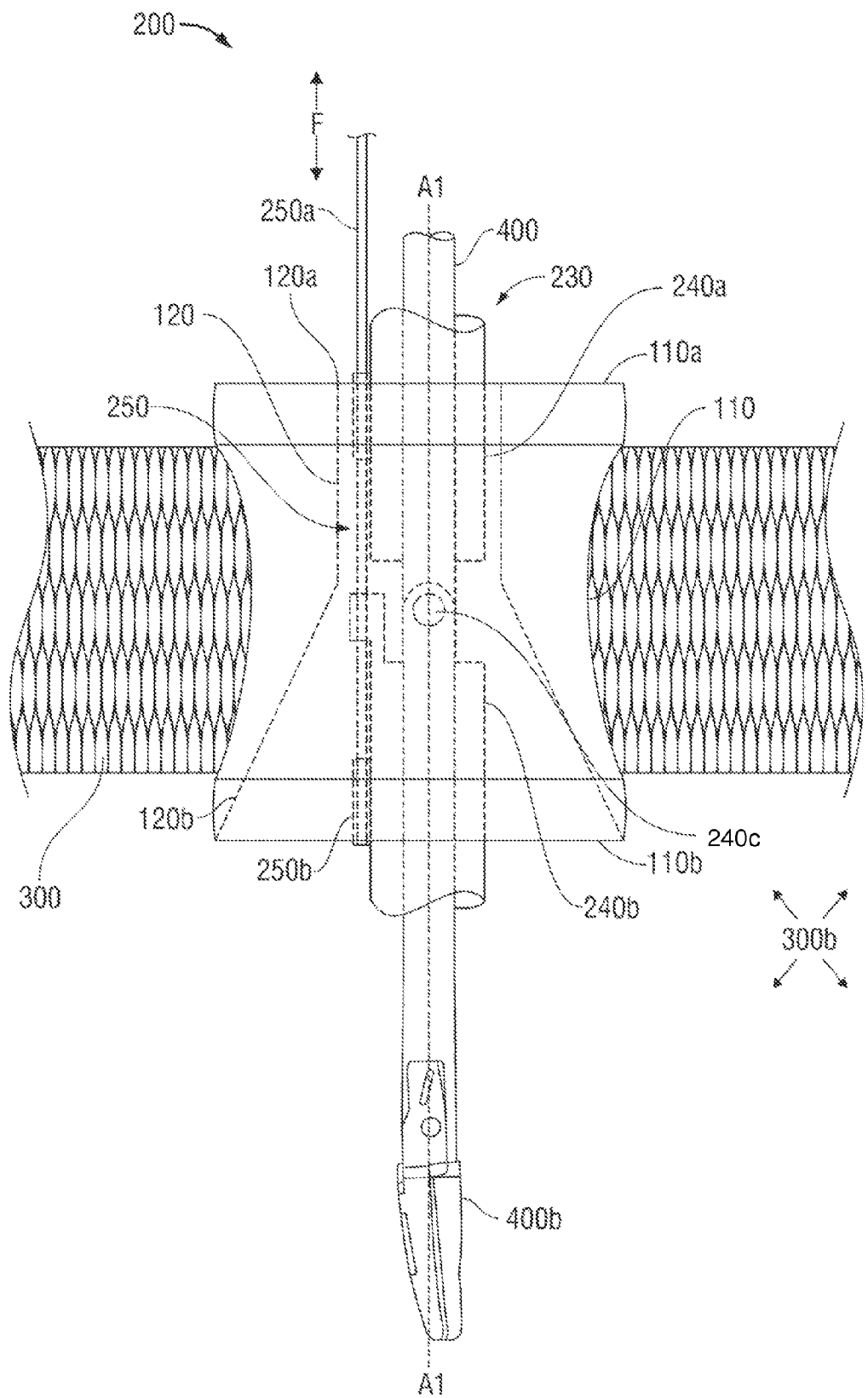
FIG. 8 is a side view of an embodiment of an articulating surgical access port having a surgical instrument inserted therethrough and additionally having a flexible pusher element.

Turning now to FIG. 8, an embodiment of an articulating surgical access port, designated 200, is shown. Similar to the articulating surgical access port 100 discussed above, articulating surgical access port 200 includes an access member 110, having a proximal end 110a and a distal end 110b, and defining a longitudinal axis A1.

The access member 110 includes at least one lumen 120 that extends from a lumen entrance 120a at the proximal end 110a of the access member 110 to the lumen exit 120b at the distal end 110b of the access member 110. The lumen 120 is configured to widen toward the distal end 110b of the access member 110, such that the lumen exit 120b of the lumen 120 is slotted.

Articulating surgical access port 200 also includes an articulation mechanism 230. The articulation mechanism 230, similar to articulation mechanism 130 discussed above, includes two tubular members 240a,b connected at a joint 240c. Disposed on the tubular members 240a,b is a flexible pusher 250. Flexible pusher 250 may be disposed on an outer surface, an inner surface, or embedded within tubular members 240a,b. Flexible pusher 250 is also fixably attached at its distal end 250b to the second tubular member 140b. Flexible pusher 250 is capable of translation along the longitudinal axis A1, and so may be slidably connected to the tubular members 240a,b at points proximal of its distal end 250b. Shown disposed through the tubular members 140a,b is surgical instrument 400 with end effector 400b.

In embodiments, the flexible pusher 250 may be disposed on the tubular members 140a,b such that a distal end 250b of the flexible pusher 250b may reverse direction at a point on the second tubular member 240b. In this configuration, the flexible pusher 250 will translate a force substantially opposite in direction to a force exerted on handle 250a by an operator of the articulating surgical access port 200.

Figure 9:
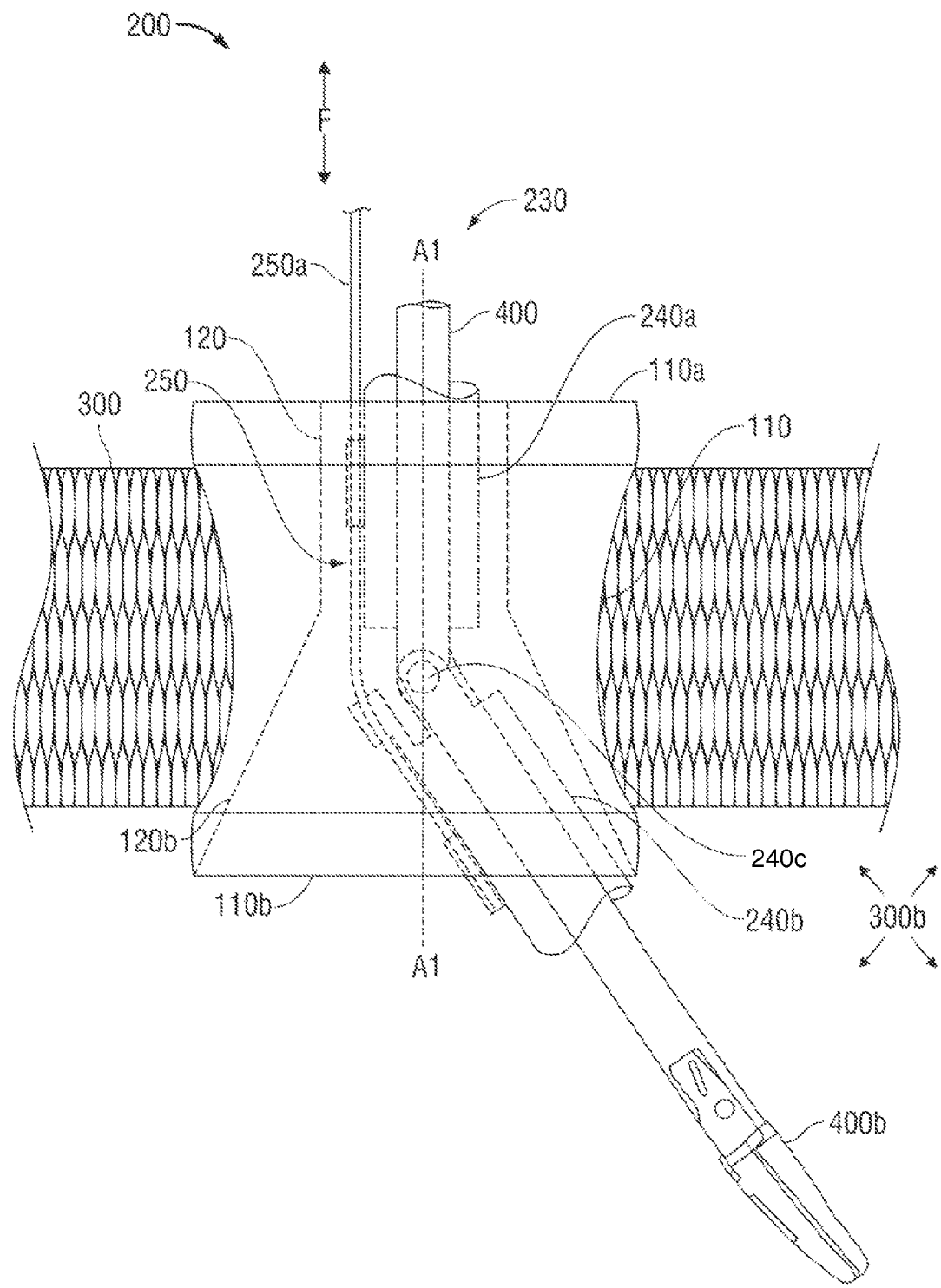
FIG. 9 is a side view of the embodiment of FIG. 8, with the articulation structure having been engaged and the surgical instrument deflected in response.

Turning now to FIG. 9, the articulating surgical access port 200 is shown with the flexible pusher 250 having been engaged by an operator, and the second tubular member 240b rotated about an axis through the joint 240c. The surgical instrument 400, disposed therethrough, is shown deflected in response to the forces exerted by the first and second tubular members 240a,b.

The lumen 120 allows for freedom of movement of the second tubular member 240b during articulation. Additionally, the widened lumen exit 120b at the distal end 110b of the access member 110 allows the surgical instrument 400 and the end effector 400b to reach points in an internal body cavity 300b laterally spaced from the longitudinal axis A1.

Figure 10:
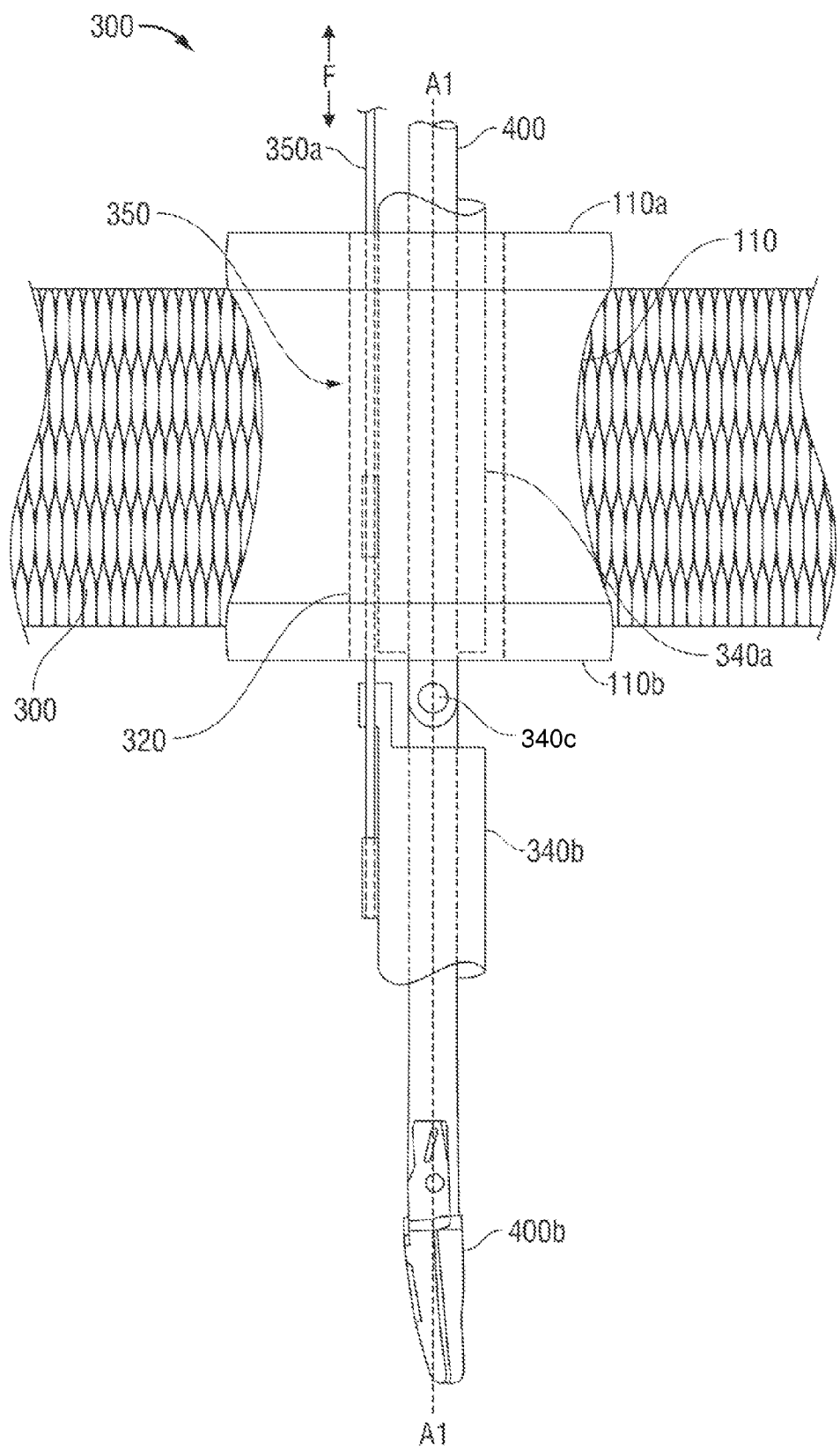
FIG. 10 is a side view of another embodiment of an articulating surgical access port having a second tubular member extending below the access member and having a surgical instrument inserted therethrough.

Referring now to FIG. 10, an embodiment of an articulating surgical access port, designated 300, is shown. The articulating surgical access port 300 is substantially similar to articulating surgical access ports 100,200 discussed above in that it includes an access member 110 having the proximal end 110a and a distal end 110b and defines a longitudinal axis A1. The access member 110 also contains a lumen 320. However, unlike the previous embodiments, the lumen 320 is not configured to accommodate movement of internal components. The articulating surgical access port 300 also contains a pair of tubular members 340a,b connected at a joint 340c. Disposed on the tubular members 340a,b is a pusher element 350, which may be rigid or flexible as discussed in the previous embodiments. The pusher element 350 may further include a handle 350a extending proximally of the access member 110. However, the articulating surgical access port 300 is configured such that the second tubular member 340b is disposed distally of and external to the access member 110. Thus, when the articulating surgical access port 300 is engaged, second tubular member 340b is free to pivot about an axis substantially transverse to the longitudinal axis A1 without the need for a shaped lumen (lumen 120, as in the previous embodiments).

It will be understood that various modifications may be made to the embodiments of the presently disclosed articulating surgical access ports. Therefore, the above description should not be construed as limiting, but merely as exemplifications of embodiments. Those skilled in the art will envision other modifications within the scope and spirit of the present disclosure.

What is claimed is:

1. A surgical access port, comprising:
   a housing comprising an access member having a proximal end and a distal end and defining a longitudinal axis;
   at least one lumen extending through the access member from the proximal to the distal end along the longitudinal axis, the at least one lumen containing at least one articulation structure, the at least one articulation structure having:
   a first tubular member,
   a second tubular member hingably attached to an end of the first tubular member, and
   an articulation element slidably attached to the first tubular member, wherein the articulation element is disposed on an outer surface of the first tubular member.

2. The surgical access port of claim 1, wherein the articulation element is a rigid member.

3. The surgical access port of claim 2, wherein the articulation element includes a first mating surface that engages a second mating surface on the second tubular member.

4. The surgical access port of claim 3, wherein the first and second mating surfaces are comprised of gear teeth.

5. The surgical access port of claim 1, wherein the articulation element includes a handle extending in a proximal direction.

6. The surgical access port of claim 1, further comprising a surgical instrument disposed through the first and second tubular members.

* * * * *